(12) United States Patent
Borges et al.

(10) Patent No.: US 9,183,603 B2
(45) Date of Patent: *Nov. 10, 2015

(54) DISPLAYING A BARCODE ON A DISPLAY OF AN INFUSION PUMP

(71) Applicant: CareFusion 303, Inc., San Diego, CA (US)

(72) Inventors: Gregory Borges, San Diego, CA (US); Jeffrey L. Gaetano, San Diego, CA (US); Daniel Vik, La Jolla, CA (US)

(73) Assignee: CareFusion 303, Inc., San Diego, CA (US)

( * ) Notice: Subject to any disclaimer, the term of this patent is extended or adjusted under 35 U.S.C. 154(b) by 118 days.

This patent is subject to a terminal disclaimer.

(21) Appl. No.: 14/062,477

(22) Filed: Oct. 24, 2013

(65) Prior Publication Data

US 2014/0048604 A1 Feb. 20, 2014

Related U.S. Application Data

(63) Continuation of application No. 13/069,347, filed on Mar. 22, 2011, now Pat. No. 8,567,681.

(51) Int. Cl.
| | |
|---|---|
| *G06K 19/00* | (2006.01) |
| *G06Q 50/24* | (2012.01) |
| *G06K 19/06* | (2006.01) |
| *G06F 19/00* | (2011.01) |

(52) U.S. Cl.
CPC ............ *G06Q 50/24* (2013.01); *G06F 19/3406* (2013.01); *G06F 19/3468* (2013.01); *G06F 19/36* (2013.01); *G06K 19/06112* (2013.01); *A61M 2205/6063* (2013.01)

(58) Field of Classification Search
USPC .......................................................... 235/462
See application file for complete search history.

(56) References Cited

U.S. PATENT DOCUMENTS 8,567,681 B2 * 10/2013 Borges et al. ............ 235/462.13

* cited by examiner

*Primary Examiner* — Matthew Mikels
(74) *Attorney, Agent, or Firm* — Fred C. Hernandez; Mintz Levin Cohn Ferris Glovsky and Popeo, P.C.

(57) ABSTRACT

An infusion pump system includes an infusion channel, and a display associated with the infusion channel. The display is for rendering a scannable barcode.

24 Claims, 5 Drawing Sheets

DISPLAYING A BARCODE ON A DISPLAY OF AN INFUSION PUMP

CROSS REFERENCE TO RELATED APPLICATION

This application is a Continuation of patent application Ser. No. 13/069,347, filed on Mar. 22, 2011, which is issuing on Oct. 29, 2013 under U.S. Pat. No. 8,567,681, entitled "Displaying A Barcode On A Display of An Infusion Pump", the contents of which are hereby fully incorporated by reference.

BACKGROUND

Use of an infusion pump in conjunction with a Bar Code Medical Administration (BCMA) system requires that the infusion pump present a barcode. Typically, this barcode is manually attached or adhered to an infusion channel of an infusion pump. This barcode is scanned to associate a medication order with the infusion channel. The use of this approach has many issues. For example, correlation of the BCMA systems identification information with that of other means (e.g., wireless networking), cleaning of the infusion pump, barcode label loss and subsequent replacement.

Moreover, the symbology, format and content of the barcode used to identify the pump channel is specific to the BCMA system used. The manufacturer of the infusion pump's barcode is not used, and there is no universal standard for the barcodes compatible with BCMA systems.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
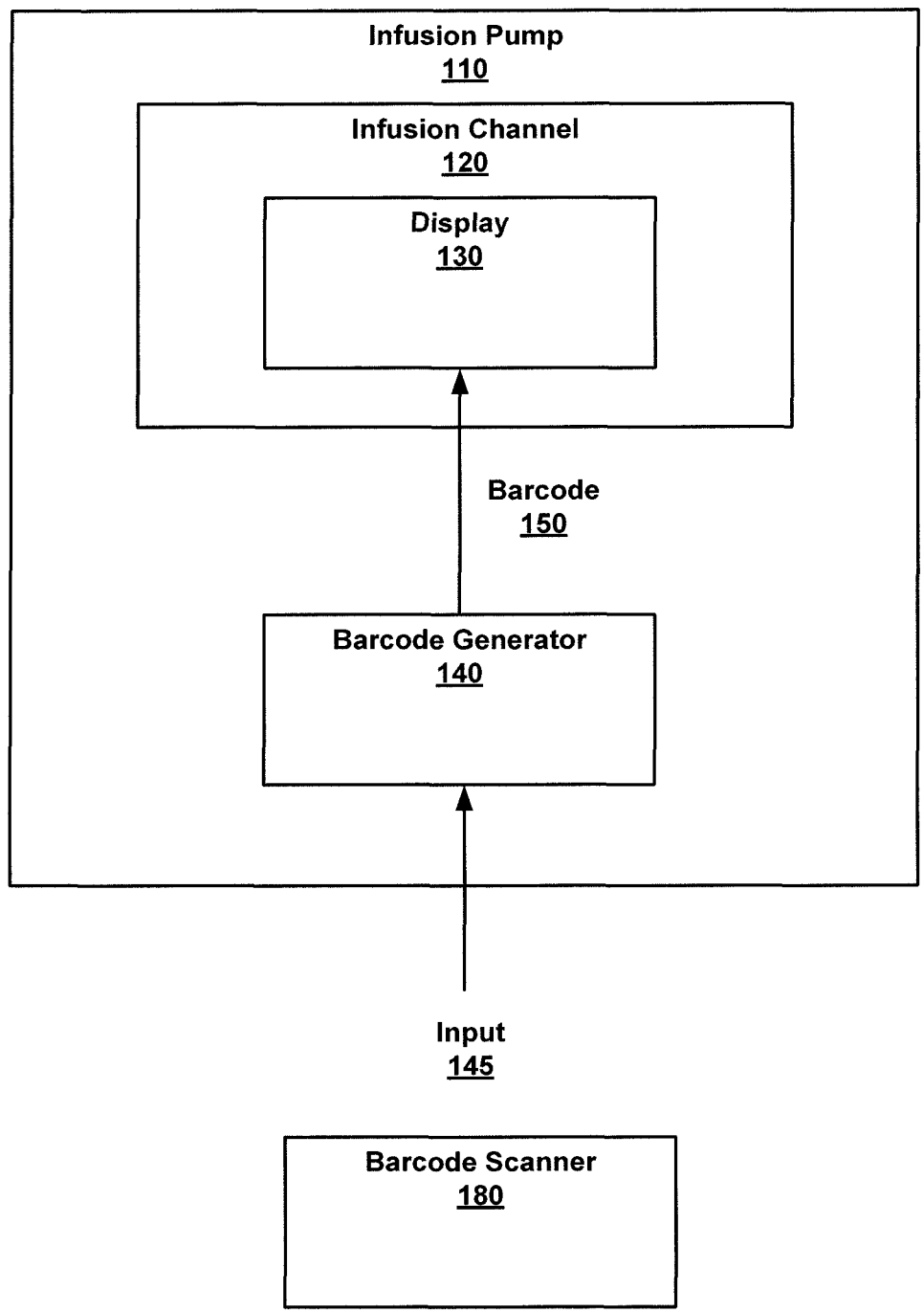
FIGS. 1-3 illustrate examples of an infusion pump system, in accordance with embodiments of the present invention.

FIG. 1 depicts an embodiment of infusion pump system 100. Infusion pump system includes infusion pump 110. Infusion pump 110 includes at least one infusion channel 120 for providing an order of medication to a patient.

Infusion pump 110 also includes at least one display 130. Display 130 is for rendering a scannable barcode 150 generated by barcode generator 140.

Additionally, display 130 displays user-readable information. For example, in addition to displaying barcode 150, display 130 also displays information such as, a name of the pump, patient name, drug dosage, etc that are able to be read by a user.

In one embodiment, display 130 is a transmissive display (e.g., backlit LCD display) with sufficient contrast and resolution such that an image scanner is able to scan barcode 150. In another embodiment, display 130 is a reflective display (e.g., electronic paper).

Barcode 150 is any optical machine-readable representation of data. For example, a 2-D barcode. In general, barcode 150 uniquely identifies infusion channel 120. For example, barcode 150 is utilized to associate infusion channel 120 to an infusion order.

In one embodiment, barcode 150 includes a Uniform Resource Locator (URL). When scanned by an appropriate configured mobile device, a browser on the mobile device is able to view the given web page associated with the URL and display its contents. Moreover, this functionality allows a user access to context-sensitive instruction material (e.g., videos, diagrams, etc.) or to information on a particular device alarm or malfunction.

Barcode 150 can be static information or dynamically changing information, which will be described in detail below.

Barcode generator 140 receives input 145 to facilitate in generating barcode 150. Input 145 can be, but is not limited to, configuration data, unique device data and system state. Barcode generator 140 assures that each barcode is compatible with the barcoding application (e.g., a BCMA system) in use.

In one embodiment, barcode generator 140 dynamically generates barcodes for display on display 130. For example, display 130 dynamically displays a first dynamic barcode when infusion pump is at a first state and dynamically displays a second dynamic barcode when infusion pump is at a second state. In another example, display 130 initially displays a barcode indicating a channel identifier, but changes to displaying a barcode indicating infusion status in response to a clinician pressing a button/key on infusion pump 110.

Unique device data is information particular to infusion pump 110 and/or infusion channel 120. For example, model number, serial number or MAC address, etc.

System state information allows barcode generator 140 to change the generated barcode that is rendered on the display to dynamically change in real-time according to the current state of infusion pump system 100.

Configuration data is information associated with the current configuration of infusion pump 110. It specifies what is to be displayed on display 130 for each applicable system state.

In one embodiment, configuration data indicates how to construct the data to be encoded into barcode 150. For example, data to be encoded may include a fixed field plus a field containing the device serial number. In another example, the barcode data could be a unique identifier generated by a particular rule from the device serial number and/or model number.

In another embodiment, configuration data includes a specification of the format, symbology and encoding used to create the barcode image from the barcode data. For example, configuration data can be configuration data from a plurality of different BCMA systems. Moreover, the configuration data can be stored on memory on infusion pump 110 or from an external configuration system.

In a further embodiment, a user specifies a configuration by selecting support for a particular BCMA system or by making lower level, more granular choices. The configuration may be applied through device settings or via a clinical dataset. Moreover, configurations may be institution wide or vary by care area.

Input 145 can include dynamic data (e.g., configuration data and/or system state) such as, but not limited to, medication order information, infusion status, drug information, dosage information, volume infused, volume remaining, patient ID, clinician ID, etc.

Accordingly, infusion pump system 100 can utilize the dynamic data to aid in charting. For example, to facilitate in populating an automated flow sheet or Electronic Medication Administration Record (eMAR). The dynamic information can be used to confirm handling of an automated order that is transmitted back to a medication administration system.

Barcode scanner 180 is for scanning barcode 150 rendered on display 130. Barcode scanner 180 can be any scanner capable of scanning barcode 150 displayed on display 130.

In one embodiment, display 130 is integrated into infusion pump 110. For example, display 130 is integrated in the form factor of infusion pump 110. In particular, display 130 is integrated into infusion channel 120.

In another embodiment, display 130 is a separate component that is attached to a legacy infusion pump or infusion channel. Accordingly, display 130 includes barcode generator 140 or is able to wirelessly receive barcode 150 from barcode generator located in another medical system.

Display 130 is disposed at a location that the correspondence between the infusion channel and the barcode is obvious to a clinician.

Figure 2A:
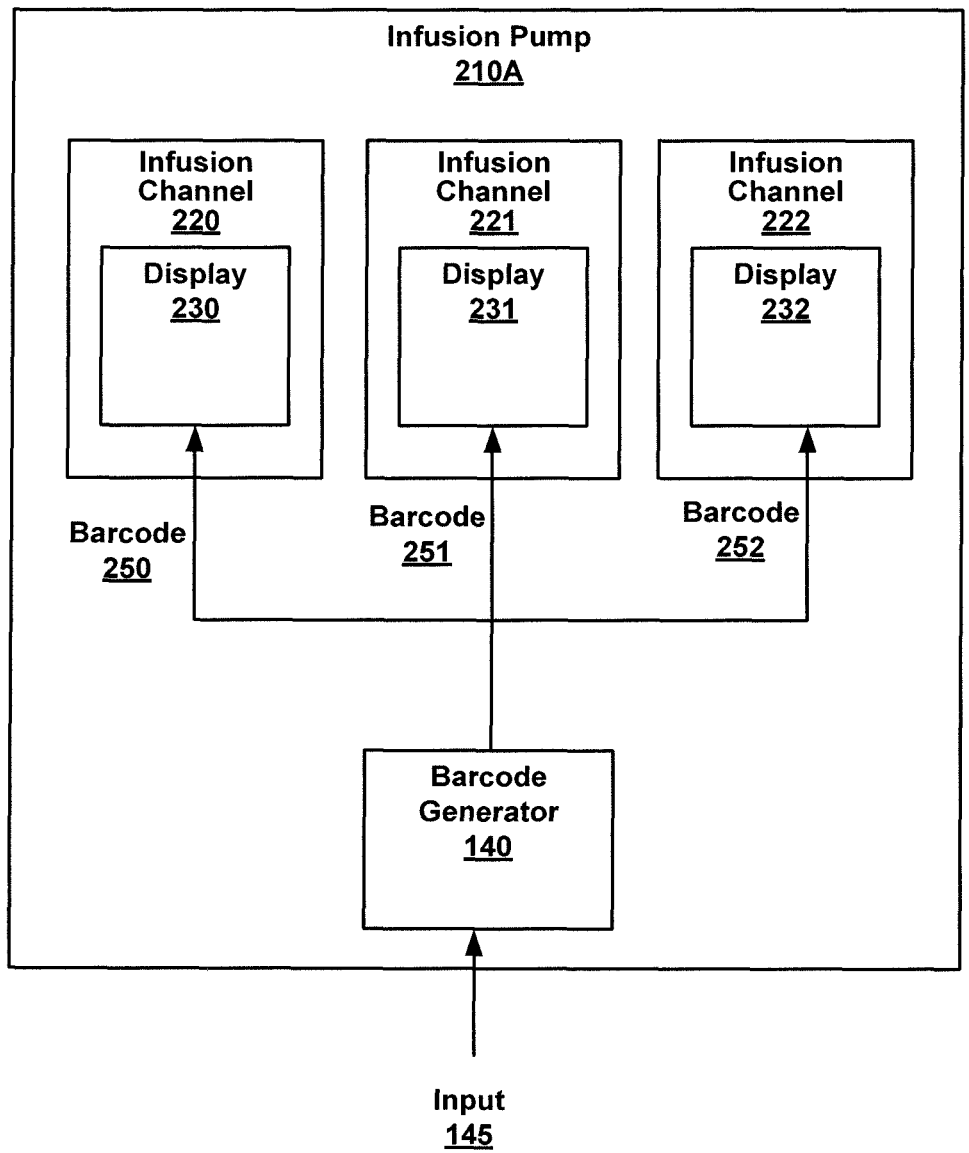

FIG. 2A depicts an embodiment of infusion pump 210A. Infusion pump 210A is similar to infusion pump 110. Accordingly, infusion pump 210A operates in a similar fashion as infusion pump 110.

However, infusion pump 210A includes infusion channels 220-222 and displays 230-232 correspondingly associated with infusion channels 220-222. It should be appreciated that infusion pump 210A can include any number of infusion channels.

In one embodiment, infusion channels 220-222 are integrated in infusion pump 210A.

Barcode generator 140 generates barcodes 250-252 that are correspondingly displayed on displays 230-232.

Figure 2B:
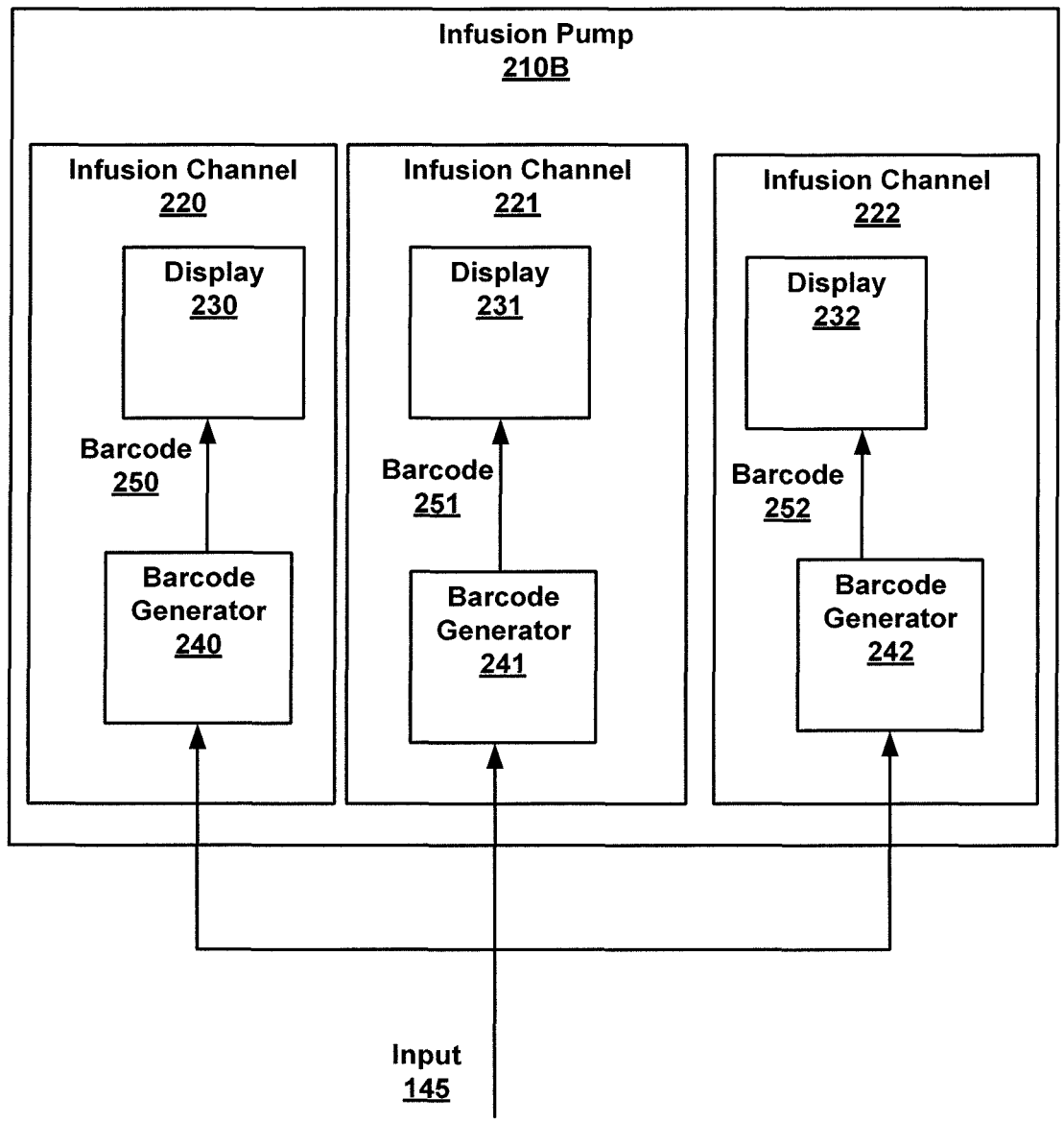

FIG. 2B depicts an embodiment of infusion pump 210B. Infusion pump 210B is similar to infusion pump 210A. Accordingly, infusion pump 210B operates in a similar fashion as infusion pump 210A.

However infusion channels 220-222 are modular components that are associated with infusion pump 210B. It should be appreciated that infusion pump 210B can include any number of infusion channels.

Barcode generators 240-242 are a part of or integrated with infusion channels 220-222, respectively.

Figure 3:
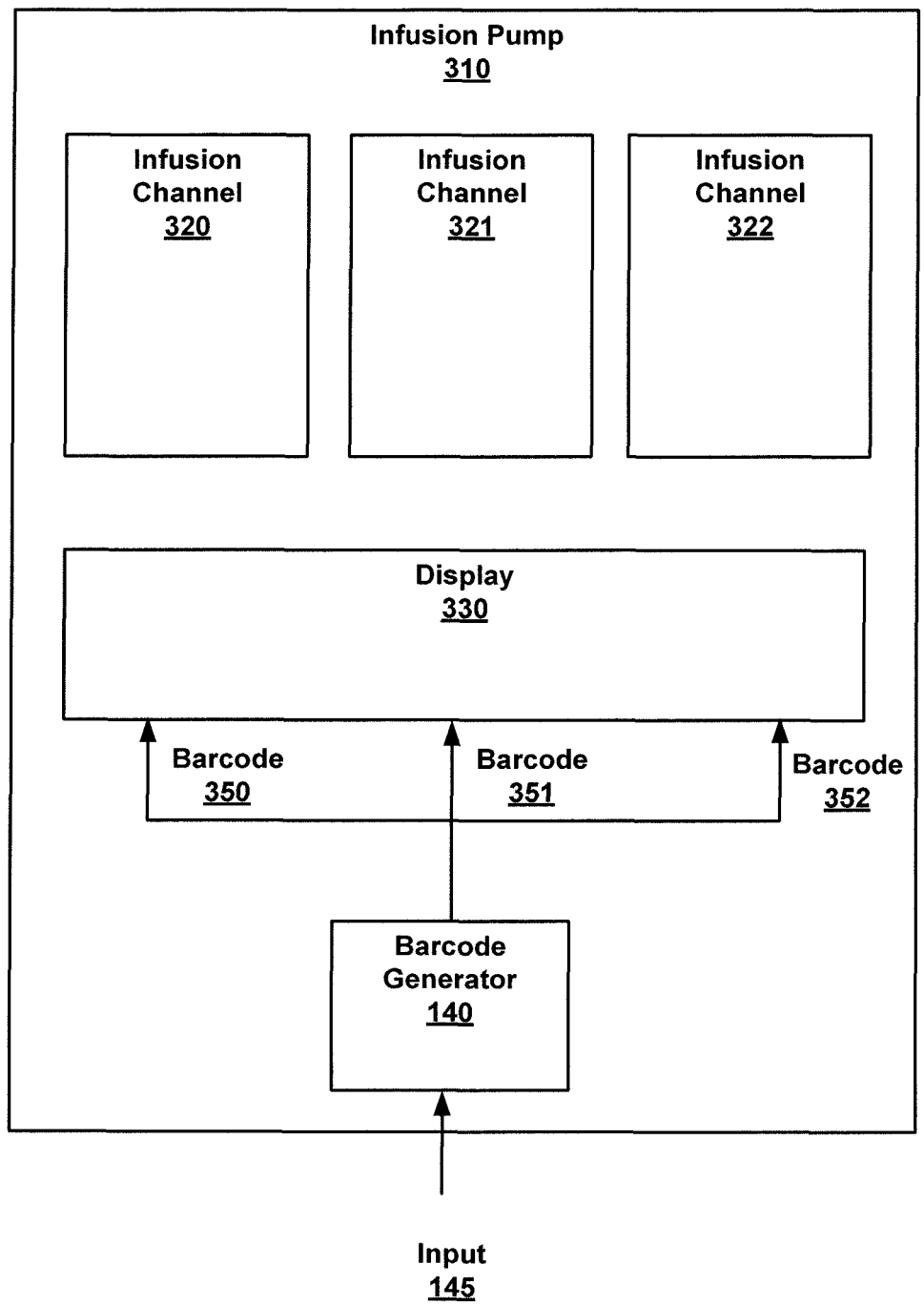

FIG. 3 depicts an embodiment of infusion pump 310. Infusion pump 310 is similar to infusion pumps 110, and 210A-B. Accordingly, infusion pump 310 operates in a similar fashion as infusion pumps 110, and 210A-B.

However, infusion pump 310 includes display 330 associated with infusion channels 320-322. In one embodiment, infusion channels 320-322 are modular infusion channels. It should be appreciated that infusion pump 310 can include any number of infusion channels.

Barcode generator 140 generates barcodes 350-352 that are associated with infusion channels 320-322, respectively. As such, display 330 is able to display a barcode associated with a selected infusion channel. For example, display 330 renders barcode 350 when infusion channel 320 is selected.

Display 330 can be integrated within infusion pump 310 or can be a separate from infusion pump 310.

Figure 4:
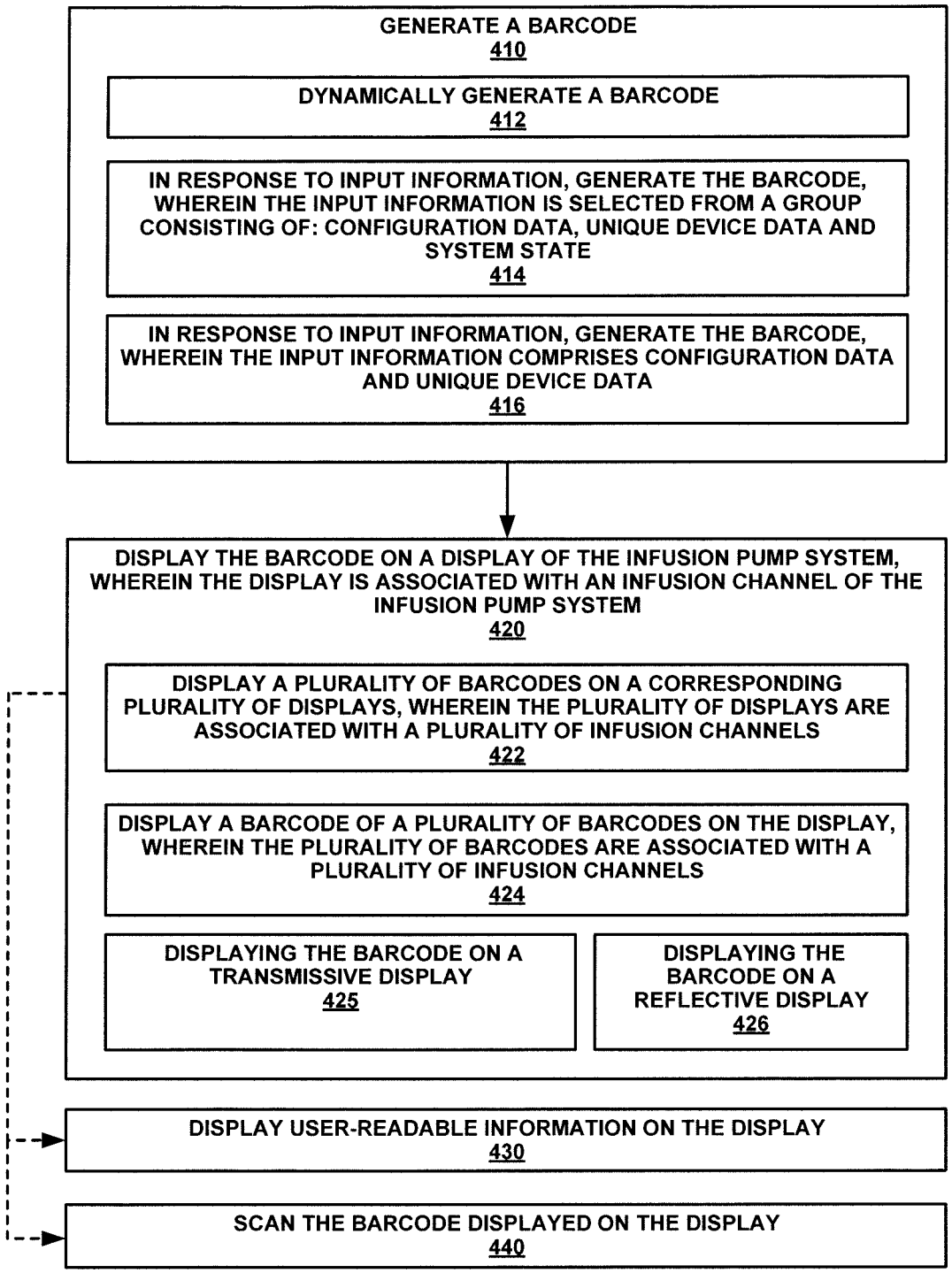
FIG. 4 illustrates an example of a method for displaying a barcode on a display of an infusion pump system, in accordance with an embodiment of the present invention.

FIG. 4 depicts an embodiment of a method 400 for displaying a barcode on a display of an infusion pump system. In various embodiments, method 400 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 400 is performed at least by infusion pumps 110, 210 and 310, as described in FIGS. 1-3.

At 410 of method 400, a barcode is generated. For example, barcode generator 140 generates barcode 150 associated with infusion channel 120.

In one embodiment, at 412, a barcode is dynamically generated. For example, barcode 150 is dynamically changed in response to a dynamically changing system state.

In another embodiment, at 414, in response to input information, the barcode is generated, wherein the input information is selected from a group consisting of: configuration data, unique device data and system state. For example, in response to input 145, barcode 150 is generated.

In a further embodiment, at 416, the barcode is generated at power up (in response to configuration data and unique device data) and displayed until the device is turned off.

At 420, the barcode is displayed on a display of the infusion pump system, wherein the display is associated with an infusion channel of the infusion pump system.

In one embodiment, at 422, a plurality of barcodes are displayed on a corresponding plurality of displays, wherein the plurality of displays are associated with a plurality of infusion channels. For example, barcodes 250-252 are correspondingly displayed on displays 230-232. Moreover, displays 230-232 are integrated with infusion channels 230-232.

In another embodiment, at 424, a barcode of a plurality of barcodes is displayed on the display, wherein the plurality of barcodes are associated with a plurality of infusion channels. For example, barcode 351 is displayed on display 330 when infusion channel 321 is selected by a user. Moreover, barcodes 350-352 are associated with infusion channels 320-322.

In further embodiments, at 425, the barcodes are displayed on a transmissive display, and at 426, the barcodes are displayed on a reflective display.

At 430, user-readable information is displayed on the display. For example, a patients name is displayed on display 150.

At 440, the barcode displayed on the display is scanned. For example, barcode scanner 180 scans barcode 150 that is displayed on display 130.

Various embodiments of the present invention are thus described. While the present invention has been described in particular embodiments, it should be appreciated that the present invention should not be construed as limited by such embodiments, but rather construed according to the following claims.

The invention claimed is:

1. A non-transitory computer program product storing instructions, which when executed by at least one data processor, result in operations comprising:
dynamically generating a series of scannable barcodes on a display of an infusion pump system in response to dynamically changing input information characterizing operation of the infusion pump system;
scanning at least a portion of the scannable barcodes to obtain infusion related data; and
populating, based on the obtained infusion related data, fields of an Electronic Medication Administration Record (eMAR).

2. A system comprising:
at least one data processor; and
memory storing instructions, which when executed by the at least one data processor, result in operations comprising:
dynamically generating a series of scannable barcodes on a display of an infusion pump system in response to dynamically changing input information characterizing operation of the infusion pump system;
scanning at least a portion of the scannable barcodes to obtain infusion related data; and
populating, based on the obtained infusion related data, fields of an Electronic Medication Administration Record (eMAR).

3. A non-transitory computer program product for displaying a barcode on a display of an infusion pump system, the computer program product storing instructions, which when executed by at least one data processor, result in operations comprising:
dynamically generating in real-time a first scannable barcode and dynamically generating in real-time a second scannable barcode in response to dynamically changing input information, wherein at least one of the first scannable barcode and the second scannable barcode comprises a Uniform Resource Locator (URL), which when activated by a mobile device scanning a barcode containing the URL, causes context-sensitive instruction material to be displayed on the mobile device;
displaying the first scannable barcode on a display of the infusion pump system; and
displaying the second scannable barcode to replace the first scannable barcode on the display.

4. The computer program product of claim 3, wherein the input information is selected from a group consisting of: configuration data, unique device data and system state.

5. The computer program product of claim 3, wherein the input information comprises: configuration data and unique device data.

6. The computer program product of claim 3, wherein the displaying the barcode on a display of the infusion pump system comprises:
displaying a plurality of barcodes on a corresponding plurality of displays, wherein the plurality of displays are associated with a plurality of infusion channels.

7. The computer program product of claim 3, wherein the displaying the barcode on a display of the infusion pump system comprises:
displaying a barcode of a plurality of barcodes on the display, wherein the plurality of barcodes are associated with a plurality of infusion channels.

8. The computer program product of claim 3, wherein the displaying the barcode on a display of the infusion pump system comprises:
displaying the barcode on a transmissive display.

9. The computer program product of claim 3, wherein the displaying the barcode on a display of the infusion pump system comprises:
displaying the barcode on a reflective display.

10. The computer program product of claim 3, wherein the operations further comprise:
displaying user-readable information on the display.

11. The computer program product of claim 3, wherein the operations further comprise:
scanning the barcode displayed on the display.

12. The computer program product of claim 3, wherein the context-sensitive instruction material comprises: at least one video to be displayed on the mobile device.

13. The computer program product of claim 3, wherein the context-sensitive instruction material comprises: at least one diagram to be displayed on the mobile device.

14. A system for displaying a barcode on a display of an infusion pump system comprising:
at least one data processor; and
memory storing instructions, which when executed by the at least one data processor, result in operations comprising:
dynamically generating in real-time a first scannable barcode and dynamically generating in real-time a second scannable barcode in response to dynamically changing input information, wherein at least one of the first scannable barcode and the second scannable barcode comprises a Uniform Resource Locator (URL), which when activated by a mobile device scanning a barcode containing the URL, causes context-sensitive instruction material to be displayed on the mobile device;
displaying the first scannable barcode on a display of the infusion pump system; and
displaying the second scannable barcode to replace the first scannable barcode on the display.

15. The system of claim 14, wherein said input information is selected from a group consisting of: configuration data, unique device data and system state.

16. The system of claim 14, wherein said input information comprises: configuration data and unique device data.

17. The system of claim 14, wherein said displaying said barcode on a display of said infusion pump system comprises:
displaying a plurality of barcodes on a corresponding plurality of displays, wherein said plurality of displays are associated with a plurality of infusion channels.

18. The system of claim 14, wherein said displaying said barcode on a display of said infusion pump system comprises:
displaying a barcode of a plurality of barcodes on said display, wherein said plurality of barcodes are associated with a plurality of infusion channels.

19. The system of claim 14, wherein said displaying said barcode on a display of said infusion pump system comprises:
displaying said barcode on a transmissive display.

20. The system of claim 14, wherein said displaying said barcode on a display of said infusion pump system comprises:
displaying said barcode on a reflective display.

21. The system of claim 14, wherein the operations further comprise:
displaying user-readable information on said display.

22. The system of claim 14, wherein the operations further comprise:
scanning said barcode displayed on said display.

23. The system of claim 14, wherein the context-sensitive instruction material comprises: at least one video to be displayed on the mobile device.

24. The system of claim 14, wherein the context-sensitive instruction material comprises: at least one diagram to be displayed on the mobile device.

\* \* \* \* \*